United States Patent
Simard

(10) Patent No.: US 9,670,483 B2
(45) Date of Patent: *Jun. 6, 2017

(54) IMMUNOGLOBULIN VARIABLE REGION LIBRARIES

(71) Applicant: XBiotech, Inc., Vancouver (CA)

(72) Inventor: John Simard, Austin, TX (US)

(73) Assignee: XBiotech, Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/248,413

(22) Filed: Aug. 26, 2016

(65) Prior Publication Data

US 2016/0362679 A1    Dec. 15, 2016

Related U.S. Application Data

(63) Continuation of application No. 14/939,454, filed on Nov. 12, 2015, now Pat. No. 9,453,217, which is a continuation of application No. 13/547,497, filed on Jul. 12, 2012, now Pat. No. 9,234,030.

(60) Provisional application No. 61/506,749, filed on Jul. 12, 2011.

(51) Int. Cl.

| | |
|---|---|
| *C12N 15/00* | (2006.01) |
| *C07H 21/02* | (2006.01) |
| *C12N 15/10* | (2006.01) |
| *C07K 16/00* | (2006.01) |
| *C07K 16/24* | (2006.01) |

(52) U.S. Cl.
CPC ........ *C12N 15/1037* (2013.01); *C07K 16/005* (2013.01); *C07K 16/24* (2013.01)

(58) Field of Classification Search
None
See application file for complete search history.

(56) References Cited

U.S. PATENT DOCUMENTS

2016/0362679 A1* 12/2016 Simard .............. C12N 15/1037

FOREIGN PATENT DOCUMENTS

| JP | 2003527399 | 9/2003 |
|---|---|---|
| JP | 2007505611 | 3/2007 |
| JP | 2008295415 | 12/2008 |
| WO | 0168682 | 9/2001 |
| WO | 2005042774 | 5/2005 |
| WO | 2010039852 | 4/2010 |

OTHER PUBLICATIONS

Dubrovskaya, V.V., et al: "Construction of a Combinatorial Immune Library of Human Single-Chain Antibodies to Orthopoxviruses and Selection of Antibodies to Recombinant prA30L of the Variola Virus," Molecular Biology, 2007, vol. 41, No. 1:173-185.

Pansri, P. et al: "A compact phage display human scFv library for selection of antibodies to a wide variety of antigens," BMC Biotechnology, 2009, vol. 9, No. 6: 1-16.

Szankasi, Philippe and D. W. Bahler: "Clinical Laboratory Analysis of Immunoglobulin Heavy Chain Variable Region Genes for Chronic Lymphocytic Leukemia Prognosis," Journal of Molecular Diagnostics, Mar. 2010, vol. 12, No. 2:244-249.

* cited by examiner

*Primary Examiner* — Michael Burkhart
(74) *Attorney, Agent, or Firm* — Stanley A. Kim

(57) ABSTRACT

Antigen-specific immunoglobulin V-regions are identified from a library of nucleic acids amplified using polymerase chain reaction using leader sequence-specific forward primers. The use of leader sequence primers allows all V-region sequences to be amplified (including those with extensive 5' end mutations) without loss of the original 5' V gene segment sequence. These libraries can be screened for antigen-specific V-regions using eukaryotic cells engineered to express the amplified V-region-encoding nucleic acids or using bacterial phage display techniques. In the latter, a second V-region library is made using a larger than conventional set of 5' V-region primers. The sequence errors introduced into the amplification products by this method are corrected using sequence information obtained in the products amplified by the V-region primers to screen the library created using the leader sequence primers. Amino acid sequence information from fragments of donor immunoglobulins can be used to assist in the identification of nucleic acids encoding the heavy and light chains of donor antibodies as well as to design primers to amplify such nucleic acids.

5 Claims, 2 Drawing Sheets

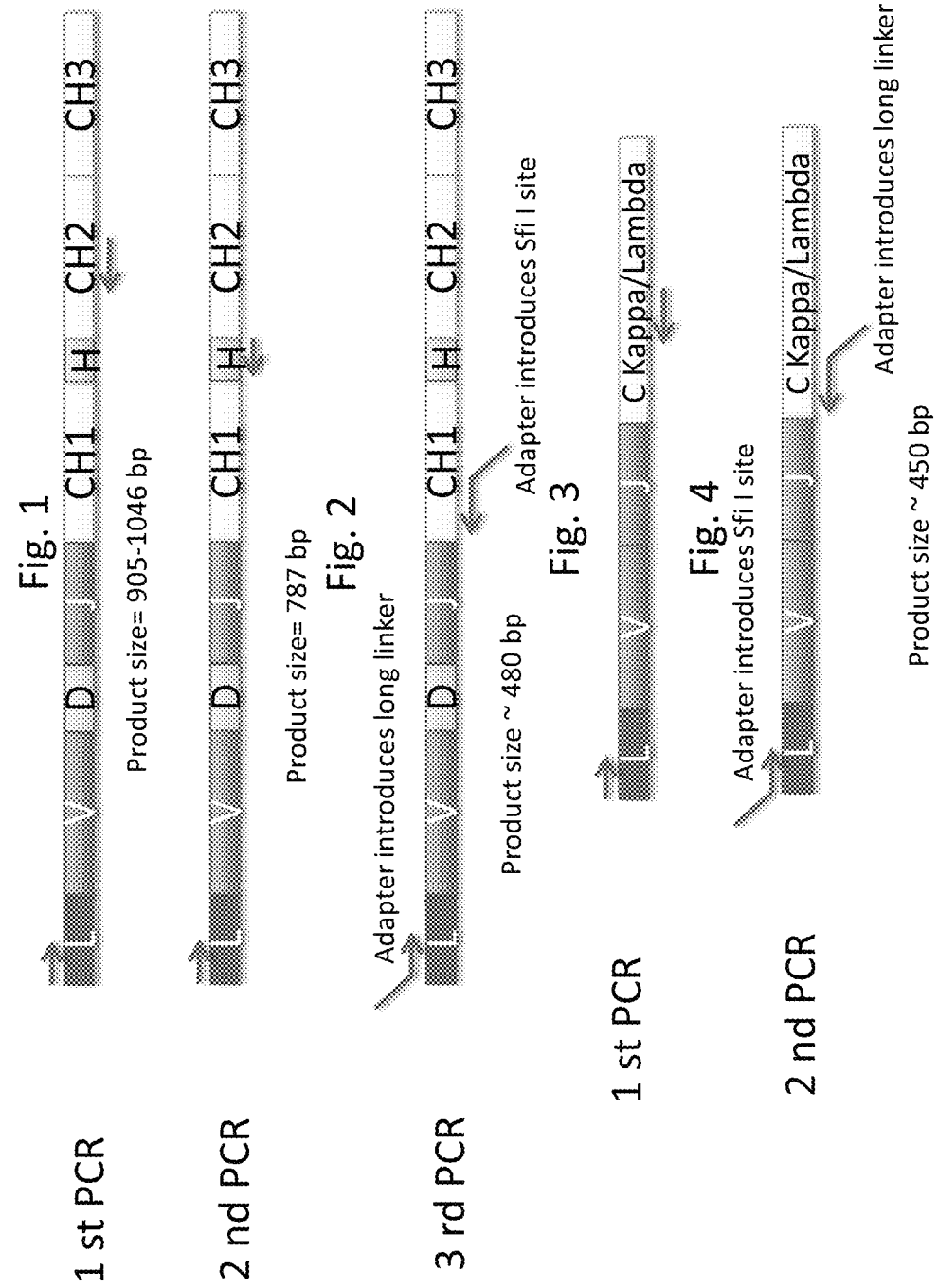

SEQUENCE LISTING

```
<160> NUMBER OF SEQ ID NOS: 178

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atggactgga cctggaggat cctcttc                                            27

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
```
atggactgga cctggaggat cctcttttg                     30

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atggactgga cctggagcat cctttttc                      27

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atggactgca cctggaggat cctc                          24

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atggactgga cctggagaat cctcttcttg                    30

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atggactgga cctggagggt cttc                          24

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atggactgga tttggaggat cctcttcttg                    30

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atggacacac tttgctccac gctc                          24

```
<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atggacacac tttgctacac gctcctg                                              27

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atggaattgg ggctgagctg gg                                                   22

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atggagttgg gactgagctg gattttcctt                                           30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atggagtttg ggctgagctg ggttttcctt                                           30

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atggagttgg ggctgagctg g                                                    21

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atggagtttg ggctgagctg gatt                                                 24
```

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atggagtttg ggctgagctg ggtttt                                          26

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atggaactgg ggctccgctg                                                 20

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atggagtttg ggctgagctg gc                                              22

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atggagtttg ggctgagctg ggtt                                            24

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atggagtttg gactgagctg ggttt                                           25

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atggagttgg ggctgtgctg g                                               21

```
<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
atggagtttg ggcttagctg ggttttc                                          27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atggagtttt ggctgagctg ggttttc                                          27

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atgacggagt ttgggctgag ctg                                              23

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atggagtttg ggctgagctg gg                                               22

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atgaaacacc tgtggttctt cctcctg                                          27

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
atgaaacacc tgtggttctt cctcctcctg                                       30

<210> SEQ ID NO 27
```

```
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atgaagcacc tgtggttctt cctcctg                                         27

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
atgaaacatc tgtggttctt ccttctcctg                                      30

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atgaagcacc tgtggttttt cctcctg                                         27

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
atggggtcaa ccgccatcct c                                               21

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
atggggtcaa ccgccatcct tg                                              22

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
atgtctgtct ccttcctcat cttcctgc                                        28

<210> SEQ ID NO 33
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
atggacatga gggtccccgc                                                    20

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
atggacatga gggtccctgc tcag                                               24

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
atggacatga gagtcctcgc tcagc                                              25

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atggacatga gggtcctcgc tcag                                               24

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
atggacatga gggtgcccgc                                                    20

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
atagacatga gggtccccgc tcag                                               24

<210> SEQ ID NO 39
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 39
atgaggctcc ctgctcagct cc                                          22

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
atgaggctcc ttgctcagct tctgg                                       25

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
atggaaaccc cagcgcagct tc                                          22

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
atggaagccc cagcgcagct                                             20

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
atggaagccc cagctcagct tct                                         23

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
atggaaccat ggaagcccca gc                                          22

<210> SEQ ID NO 45
<211> LENGTH: 29
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 45
atggtgttgc agacccaggt cttcatttc                                         29

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
atggggtccc aggttcacct cc                                                22

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
atgttgccat cacaactcat tgggtttctg                                        30

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
atggtgccct cgctgctctt tc                                                22

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
atggcctggt cccctctctt cctc                                              24

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
atggcctggt ctcctctcct cctcac                                            26

<210> SEQ ID NO 51
<211> LENGTH: 24
<212> TYPE: DNA
<213> ORGANISM: Artificial Sequence
<220> FEATURE:

<223> OTHER INFORMATION: Description of Artificial Sequence: Synthetic
    primer

<400> SEQUENCE: 51
atggccagct tccctctcct cctc                                           24

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 52
atggccggct tccctctcct cc                                             22

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 53
atgacctgct ccctctcct cctcac                                          26

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 54
atggcctggg ctctgctcct c                                              21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 55
atggcctggg ctctgctgct c                                              21

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 56
atggcctggg ctctgctatt cctcac                                         26

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
atggcatgga tccctctctt cctcggc                                              27

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
atggcctgga ccgctctcct tctg                                                 24

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
atggcctgga cccctctcct gc                                                   22

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
atggcctgga tccctctcct gctc                                                 24

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
atggcctgga cccctctctg gc                                                   22

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
atggcctgga ccgttctcct cctc                                                 24

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 63
atggcatggg ccacactcct gc                                                   22

<210> SEQ ID NO 64
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
atggcctgga tccctctcct tctccc                                               26

<210> SEQ ID NO 65
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
atggcctggg tctccttcta cctactgc                                             28

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
atggcctgga cccaactcct cctc                                                 24

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
atggcctgga ccccactcct cc                                                   22

<210> SEQ ID NO 68
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
atggcttgga ccccactcct cttcctc                                              27

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
atggcctgga ctcctcttct tctcttgctc                                              30

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
atggcctgga ctcctctcct cctcc                                                   25

<210> SEQ ID NO 71
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
atggcctgga ctcttctcct tctcgtgc                                                28

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
atggcctggg ctccactact tctcacc                                                 27

<210> SEQ ID NO 73
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
atggcctgga ctcctctctt tctgttcctc                                              30

<210> SEQ ID NO 74
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
atggcctgga tgatgcttct cctcggac                                                28

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75

```
atggcctggg ctcctctgct c                                              21
```

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76

```
atgccctggg ctctgctcct c                                              21
```

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77

```
caggtkcagc tggtgcagtc tgg                                            23
```

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78

```
caggtccagc ttgtgcagtc tgg                                            23
```

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79

```
saggtccagc tggtacagtc tgg                                            23
```

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80

```
caratgcagc tggtgcagtc tgg                                            23
```

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81

```
<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
caggtcacct garggagtc tgg                                                  23

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
cgggtcacct gagggagtc tgg                                                  23

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gargtgcagc tggtggagtc tgg                                                 23

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
caggtgcagc tggtggagtc tgg                                                 23

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gaggtgcagc tgttggagtc tgg                                                 23

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gaggtgcagc tggtggag                                                       18
```

(first line continued from previous page:)
```
cagatcacct tgaaggagtc tgg                                                 23
```

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
caggtgcagc tgttggagtc tgg                                           23

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gaggtgcagc tggtggagtc tgc                                           23

<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gaggtgcagc tggtggagac tgg                                           23

<210> SEQ ID NO 91
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gaggtgcagc tggtggagtc tcg                                           23

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
cagstgcagc tgcaggagtc sgg                                           23

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
caggtgcagc tacagcagtg ggg                                           23

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 94
caggtgcagc tgcaggactc ggg     23

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 95
caggtgcggc tgcaggagtc ggg     23

<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 96
gargtgcagc tggtgcagtc tgg     23

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 97
caggtacagc tgcagcagtc agg     23

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 98
caggtscagc tggtgcaatc tgg     23

<210> SEQ ID NO 99
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 99
cctggccggc ctggccacta gtgaccgatg ggcccttggt gga     43

```
<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
atccagatga cccagtctcc                                                   20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
atccagttga cccagtctcc                                                   20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
atccrgatga cccagtctcc                                                   20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
atctggatga cccagtctcc                                                   20

<210> SEQ ID NO 104
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
attgtgatga cccagactcc ac                                                22

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
rttgtgatga ctcagtctcc actc                                              24

<210> SEQ ID NO 106
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
attgtgatga cccagactcc ac                                              22

<210> SEQ ID NO 107
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
attgtgttga crcagtctcc ag                                              22

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
atagtgatga cgcagtctcc ag                                              22

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
attgtaatga cacagtctcc ascc                                            24

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
atcgtgatga cccagtctcc                                                 20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
acgacactca cgcagtctcc                                                 20

<210> SEQ ID NO 112
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
attgtgctga ctcagtctcc agac                                          24

<210> SEQ ID NO 113
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
gttgtgatga cacagtctcc agct                                          24

<210> SEQ ID NO 114
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
ggaagatcta gaggaaccac cgaagacaga tggtgcagcc acagt                   45

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
tctgtgctga ctcagccrcc                                               20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
tctgtgytga cgcagccrcc                                               20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
tctgtcgtga cgcagccrcc                                               20

<210> SEQ ID NO 118
<211> LENGTH: 23
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 118
tctgccctga ctcagcctss ctc                                              23

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
tatgwgctga ctcagccacy c                                                21

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
tatgagctga cacagcyacc                                                  20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
tctgagctga ctcaggaccc                                                  20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
tatgagctga tgcagccacc                                                  20

<210> SEQ ID NO 123
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
tatgagctga cacagccatc ctc                                              23

<210> SEQ ID NO 124
<211> LENGTH: 23
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 124
tatgagctga ctcagccaca ctc                                              23

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
tctgggccaa ctcaggtgcc                                                  20

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
cytgtgctga ctcaatcryc c                                                21

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
cctgtgctga ctcagccccc                                                  20

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
tttatgctga ctcagcccca c                                                21

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
rctgtggtga ctcaggagcc                                                  20

<210> SEQ ID NO 130
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 130
actgtggtga cccaggagcc                                                    20

<210> SEQ ID NO 131
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
sctgtgctga ctcagccrbc ttcc                                               24

<210> SEQ ID NO 132
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
cctgtgctga ctcagccaac ctcc                                               24

<210> SEQ ID NO 133
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
ggaagatcta gaggaaccac ccgtggggtt ggccttgggc tgacc                        45

<210> SEQ ID NO 134
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
ggaagatcta gaggaaccac ccgaggggc agccttgggc tgacc                         45

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
ccaccaccac gcaygtgacc                                                    20

<210> SEQ ID NO 136
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 136
cttctccacg gtgctcccctt catgcg                                          26

<210> SEQ ID NO 137
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
acccgattgg agggcgttat ccacct                                           26

<210> SEQ ID NO 138
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
tgtgtgagtt ttgtcacaag atttgggctc                                       30

<210> SEQ ID NO 139
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
cggtgggcac tcgacacaac atttgcgctc                                       30

<210> SEQ ID NO 140
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
agttgtgtca ccaagtgggg ttttgagctc                                       30

<210> SEQ ID NO 141
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
tgatgggcat gggggaccat atttggactc                                       30

<210> SEQ ID NO 142
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 142
gggcccaggc ggccracatc cagatgaccc agtctcc                              37

<210> SEQ ID NO 143
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gggcccaggc ggccgmcatc cagttgaccc agtctcc                              37

<210> SEQ ID NO 144
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
gggcccaggc ggccgccatc crgatgaccc agtctcc                              37

<210> SEQ ID NO 145
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
gggcccaggc ggccgtcatc tggatgaccc agtctcc                              37

<210> SEQ ID NO 146
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
gggcccaggc ggccgatatt gtgatgaccc agactccac                            39

<210> SEQ ID NO 147
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
gggcccaggc ggccgatrtt gtgatgactc agtctccact c                         41

<210> SEQ ID NO 148
<211> LENGTH: 39
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 148
gggcccaggc ggccgagatt gtgatgaccc agactccac                                    39

<210> SEQ ID NO 149
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
gggcccaggc ggccgaaatt gtgttgacrc agtctccag                                    39

<210> SEQ ID NO 150
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
gggcccaggc ggccgaaata gtgatgacgc agtctccag                                    39

<210> SEQ ID NO 151
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
gggcccaggc ggccgaaatt gtaatgacac agtctccasc c                                 41

<210> SEQ ID NO 152
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
gggcccaggc ggccgacatc gtgatgaccc agtctcc                                      37

<210> SEQ ID NO 153
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
gggcccaggc ggccgaaacg acactcacgc agtctcc                                      37

<210> SEQ ID NO 154
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
```

```
gggcccaggc ggccgaaatt gtgctgactc agtctccaga c                 41
```

<210> SEQ ID NO 155
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155

```
gggcccaggc ggccgatgtt gtgatgacac agtctccagc t                 41
```

<210> SEQ ID NO 156
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156

```
gggcccaggc ggcccagtct gtgctgactc agccrcc                      37
```

<210> SEQ ID NO 157
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157

```
gggcccaggc ggcccagtct gtgytgacgc agccrcc                      37
```

<210> SEQ ID NO 158
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158

```
gggcccaggc ggcccagtct gtcgtgacgc agccrcc                      37
```

<210> SEQ ID NO 159
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159

```
gggcccaggc ggcccagtct gccctgactc agcctssctc                   40
```

<210> SEQ ID NO 160
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
gggcccaggc ggcctcctat gwgctgactc agccacyc         38

<210> SEQ ID NO 161
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
gggcccaggc ggcctcctat gagctgacac agcyacc         37

<210> SEQ ID NO 162
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
gggcccaggc ggcctcttct gagctgactc aggaccc         37

<210> SEQ ID NO 163
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
gggcccaggc ggcctcctat gagctgatgc agccacc         37

<210> SEQ ID NO 164
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
gggcccaggc ggcctcctat gagctgacac agccatcctc         40

<210> SEQ ID NO 165
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
gggcccaggc ggcctcctat gagctgactc agccacactc         40

<210> SEQ ID NO 166
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
gggcccaggc ggcctcctct gggccaactc aggtgcc         37

<210> SEQ ID NO 167
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
gggcccaggc ggcccagcyt gtgctgactc aatcrycc                           38

<210> SEQ ID NO 168
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
gggcccaggc ggccctgcct gtgctgactc agccccc                            37

<210> SEQ ID NO 169
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
gggcccaggc ggcccagsct gtgctgactc agccrbcttc c                       41

<210> SEQ ID NO 170
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
gggcccaggc ggcccagcct gtgctgactc agccaacctc c                       41

<210> SEQ ID NO 171
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
gggcccaggc ggccaatttt atgctgactc agccccac                           38

<210> SEQ ID NO 172
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
gggcccaggc ggcccagrct gtggtgactc aggagcc                            37

```
<210> SEQ ID NO 173
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
gggcccaggc ggcccagact gtggtgaccc aggagcc                                37

<210> SEQ ID NO 174
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
gggcccaggc ggcccagcct gtgctgactc agccacc                                37

<210> SEQ ID NO 175
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
gggcccaggc ggcccaggca gggctgactc agccacc                                37

<210> SEQ ID NO 176
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
ggtggttcct ctagatcttc ctcctctggt ggcggtggct cgggcggtgg tggg             54

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
cctgtgctga ctcagccacc                                                   20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
gcagggctga ctcagccacc                                                   20
```

IMMUNOGLOBULIN VARIABLE REGION LIBRARIES

CROSS-REFERENCE TO RELATED APPLICATIONS

This application is a continuation of U.S. nonprovisional patent application Ser. No. 14/939,454 filed on Nov. 12, 2015, which is a continuation of U.S. nonprovisional patent application Ser. No. 13/547,497 filed on Jul. 12, 2012 (now U.S. Pat. No. 9,234,030) which claims priority from U.S. provisional patent application No. 61/506,749 filed on Jul. 12, 2011.

SEQUENCE LISTING

The instant application contains a Sequence Listing which has been submitted in ASCII format via EFS-Web and is hereby incorporated by reference in its entirety. Said ASCII copy, created on Jul. 12, 2012, is named 54070120.txt and is 40,626 bytes in size.

FIELD OF THE INVENTION

The invention relates generally to the fields of immunology and molecular biology. More particularly, the invention relates to methods, compositions, and kits for identifying "affinity-matured" human antibodies (Abs) containing somatic hypermutations.

BACKGROUND

Throughout the $19^{th}$ and $20^{th}$ centuries, scientists and physicians dreamt of being able to custom design therapeutic agents that were highly specific for a single biological target. By selectively attacking disease while sparing healthy tissue, these "magic bullets" were thought to be ideal therapeutic agents. It was not until the early 1970's, however, that this dream began to be realized when Kohler and Milstein (Nature 256: 495, 1975) developed a groundbreaking method for making antigen (Ag)-specific monoclonal antibodies (mAbs). This was perhaps one of the most significant events in the history in modern immunology. Using this new approach, numerous research, diagnostic, and therapeutic products were developed with a combined market of hundreds of billions of dollars.

In Kohler and Milstein's method, rodent B cells which each express a unique immunoglobulin (Ig) (i.e., a mAb) were immortalized by fusion with a myeloma cell. The ability of these mAb-secreting "hybridomas" to replicate ad infinitum allowed those that produced a mAb with high affinity for a given Ag to be selected as an engine for producing large quantities of identical mAbs. MAbs made by this method eventually were used as human therapeutics. While effective, the use of therapeutic rodent mAbs was soon discovered to be less than ideal because, after multiple administrations, they induced anti-rodent Ig immune responses, which neutralized the activity of the mAb and frequently caused serious adverse reactions in treated patients.

Attempts were therefore made to adapt Kohler and Milstein's rodent method to make human mAbs by fusing human B cells to myeloma cells. This "human hybridoma" technique proved to be more challenging than expected for a number of different reasons. First, for ethical or medical reasons, it was often difficult to increase the frequency of Ag-specific B cells by repeatedly immunizing human subjects with an Ag. Second, also for ethical or medical reasons, it was not practical to isolate human spleen tissue to obtain B cells as was done in rodents. Third, immortalized mAb-producing human cell lines were not easy to establish and tended to produce very little mAb. And fourth, because the human immunoglobulin diversity, or repertoire, of individual Ab specificities is much higher than the rodent repertoire ($\sim 10^{12}$ vs. $\sim 10^7$ individual specificities), and because the screening methodology employed was limited to no more than about $10^4$ specificities in a given sampling, it is much more technically difficult to isolate human mAb-secreting cells of a desired specificity. Identifying mAbs having low frequency specificities by this technique thus remains a daunting, "finding a needle in the haystack" effort.

In parallel with the development of "human hybridoma" methods, scientists also began attempting to "humanize" rodent antibodies by replacing various rodent amino acid sequences with those from human antibodies. In a typical application, murine Ig variable regions are combined with human constant domains, or murine complementarity determining regions (CDRs) are grafted onto a human Ig framework. This new recombinant nucleic acid construct is inserted into an expression vector which is transfected into host cells that can produce large quantities of the chimeric mAb when cultured. While this technique has done much to improve the usefulness of mAbs in therapeutic applications (by reducing the human anti-rodent-immunoglobulin response), the remaining rodent sequences can still cause the development of an undesirable anti-mAb response [e.g., a HAMA (human anti-mouse antibody) response] that can neutralize the mAb or even cause a serious adverse reaction in a patient.

Another approach for producing human mAbs has been to use chimeric animals wherein the host animal's Ig genes have been replaced, in part, with their human counterpart. Upon vaccination, these knockout/knockin animals produce human Abs and their B cell-containing spleens can be used to make human mAbs using the conventional hybridoma technique. Shortcomings that have been associated with this technology include: reduced diversity (specificity) and affinity due to an incomplete repertoire of human Ig-related genes; humoral responses that are not purely human ("humanized" transgenic animals retain their native T cells and have "leaky" expression of murine antibody responses); the antibodies produced have non-human glycosylation patterns (e.g., Galα 1-3Gal containing oligosacarides in the humanized animals are not commonly found in humans and are thus recognized as foreign); and antibodies that undergo development in an animal are not "selected" for tolerance in a human—thus even though derived from partial human sequences, they are not necessarily non-immunogenic in humans (i.e., not true human).

The advent of polymerase chain reaction (PCR) methods made it possible to amplify entire or parts of Ig genes, and allowed the creation of libraries of plasmids containing cDNAs encoding heavy and light Ig chain variable regions (V-regions) from peripheral blood leukocytes (PBLs) to be produced. Traditionally, library generation for phage display involved a set of 6 primers in the variable region of heavy chain, 4 primers in the variable region of kappa chain, and 9 primers in the variable region of lambda chain. (as described in Barbas et al., Phage Display: A Laboratory Manual. Cold Spring Harbor, 2001.) The plasmids from these libraries can be used to transfect bacteria or other host cells (e.g., yeast) which can then be screened for Ag-specific Ig components. In the phage display approach, human Ig V-region genes are cloned into bacteriophage in order to display Ab fragments on the surfaces of bacteriophage particles. Genes from extensive human Ab gene libraries are inserted into a library of phage. Each phage can potentially carry the gene for a different V-region and displays a different V-region on its surface. Commonly these phage are used to display on a bacteriophage surface an Ab construct made up of heavy and light Ig chain V-regions separated by a linker (a single chain fragment variable Ab or scFv), such that each heavy and light chain V-regions can bind a target antigen in a manner that closely mimics how a mAb binds Ag. Similar to phage display, in yeast display, Ig components are displayed as a fusion to the Aga2p protein on the surface of yeast in a manner that projects the fusion protein away from the cell surface. Flow cytometry can then be used to select those yeast cells expressing an Ig component that reacts with a target Ag. Once identified by phage or yeast display, the expressed heavy and/or light chain V-regions genes are recovered and inserted into a full-length heavy and/or light chain expression vectors. Culturing host cells transfected with such vectors allows large quantities of a mAb to be produced.

The primary benefit of phage or yeast display techniques is that huge libraries, incorporating as many as 100 billion distinct V-regions, may be screened for Ag reactivity. A drawback of these techniques is that the V-regions isolated in the first round of display are typically of very low affinity. A common reason for generating low affinities antibodies is the result of the loss of crucial hypermutated sequences (which create the mature high affinity antibodies) using this method. B lymphocytes that produce high affinity antibodies have generally undergone a process known as somatic hypermutation. In this process, germline encoded V-region sequences undergo genetic mutations, such that the gene sequence of the V-region is altered. This can result in the production of a "mature," V-region sequence that has substantially higher-affinity for a given antigen. It is generally understood that somatic hypermutation is a fundamentally important event for generating antibody diversity and high affinity antibodies. This somatic hypermutation cannot be found in the germline genomic sequences, and is represented only in a unique B lymphocyte clone.

The generation of low affinity antibodies using the phage display approach has been a major limitation to this method. This difficulty has indeed resulted in the development of many other complex approaches, including humanized mice and in vitro somatic hypermutation, as described above. Antibodies in humans undergo a selection process that makes them tolerated in the human body. These techniques result in the use of antibody sequences that are not based on human in vivo selection processes, and thus these antibodies can be immunogenic in humans. In any event, overcoming the production of low-affinity antibodies has been a major challenge for these methods.

A reason why phage display commonly generates low affinity antibodies is that it involves the use of primer sequences that are based on germline V-region sequences. There exist two possible outcomes from using V-region primers based on germline sequences: (1) the primers will fail to hybridize with somatically mutated sequences, since the mismatch between the primer and hypermutated sequences fails to result in primer annealing; or, (2) the mismatch between the primer and hypermutated sequences is conservative, such that annealing does occur, but the amplification results in recapitulation of the germline-sequence encoded by the primer rather than the underlying hypermutated sequence. In either event, since the phage display methodology involves crucial PCR amplification steps using PCR primer sequences that encode germline V-region sequences, and since these primers amplify the Ig sequences from inside the antibody V-regions, cDNA libraries generated using germline primer sequences will not contain the full repertoire of somatic hypermutated sequences. Furthermore, and importantly, the repertoire will be completely devoid of antibodies with hypermutation in the 5' end of the V-region, i.e., the region encoded by the germline encoded primer.

In other words, using primers based on germline sequences recapitulates the germline V-region sequences, thereby losing hypermutations in the area encoded by the primer sequence. This method thus systematically eliminates hypermutation in these areas of the V-region and results in an overall loss of hypermutated antibody sequences. In the case of low frequency Abs (i.e., less than 0.1, 0.01, 0.001, 0.0001, or 0.00001% of a subject's entire repertoire of Ag specificities), for which the phage display system is arguably most suited, finding V-region genes that can be used to make a high affinity mAb becomes all the more challenging.

SUMMARY

The invention is based on the development of an improved method of identifying Ag-specific Ig V-regions that occur in low frequencies in human Ab repertoires such that these V-regions can be used to make Ag-specific human mAbs or other Ag-targeting constructs. The invention also allows the identification of more complete V-region libraries, particularly those that encode antibody sequences that contain crucial somatic mutations for generating high affinity antibodies.

The development of this improved method was based on the surprising discovery that traditional phage and yeast display methods allow many of the V-regions in human peripheral blood mononuclear cells (PBMCs) that have high affinity for a target Ag to escape identification. In traditional phage and yeast display methods, PCR is used to amplify nucleic acid sequences corresponding to the V-regions of heavy and/or light Ig chains. The forward primers that initiate the PCR amplification process have a nucleic acid sequence that is complementary to the 5' germline end of each V-region so that cDNAs encoding the V-regions will be amplified.

Due to the several processes responsible for the generation of Ab diversity, the amino acid sequences of V-regions of mature Abs differ from germline sequences and from each other. Ig gene segments in mammals are arranged in groups of variable (V), diversity (D), joining (J), and constant (C) exons. The DNA for the human heavy chain includes about 50 functional VH segments, 30 DH segments, and 6 JH segments. The kappa chain includes about 40 functional Vκ segments, five Jκ segments, and 1 Cκ segment. The lambda chain DNA contains 30 Vλ segments, and 4 each of Jλ and Cλ segments. Junctional diversity results from the imprecise joining of gene segments, and during recombination, non-template nucleotides may be added between adjoining gene segments by terminal deoxynucleotidyl transferase, and become a part of the complementarity determining region (CDR). The assembled V-D-J or V-J segments then get diversified by stepwise incorporation of single nucleotide substitutions (somatic hypermutation) leading to greater antibody diversity and affinity maturation.

The three CDR regions on each V-region heavy and light chain show the most sequence diversity. Because of this diversity, these regions are also called hypervariable regions.

The six CDRs of the heavy and light chains are crucial to determining the Ag-binding specificity of an Ab. Because the 5' germline end of each V-region is not within a hypervariable region, the conventional method of using a forward primers directed to germline sequences at this site was not believed to be problematic. And indeed, for identifying those V-regions in high frequency human Abs, this method has proved to be very useful.

In work leading up to the invention, attempts were made to identify low frequency Abs. Although Abs of the desired specificity could be identified in peripheral blood samples using techniques such as ELISA (enzyme-linked immunosorbent assay), when these samples were used in conventional phage display methods, no high affinity Abs could be generated. This is a general problem in the industry and complex in vitro methods of making mutations to create combinatorial libraries of V-regions have been developed. These methods are difficult, laborious, and do not necessarily produce antibodies that maintain native human sequences.

This invention stems from troubleshooting the reasons for the failure of the phage system to generate high affinity antibodies for these low frequency antibodies. While considering their previous experiments showing that (a) there is a considerable rate of mutation away from germline in the amino acid sequence in the 5' end of V-regions and (b) two amino acid substitutions in the sections of V-regions outside the CDRs had a significant effect on an Ab's affinity for Ag, there was the startling realization that the conventional method of amplifying V-region sequences using primers for 5' germline end sequences resulted in libraries that were missing many of those V-regions that have mutations at their 5' end, and also introduced sequence errors in this area during the PCR process. Even under stringent PCR conditions, the germline sequence primers cross-hybridize with V-regions that contain some number of somatic mutations. Thus the primers, when amplifying the V-region, recapitulate the germline sequence in the cDNA. The somatic hypermutations of the true high-affinity V-region will thus be lost. Importantly, it was also realized that it was those missing V-regions that would be expected to be included in the highest affinity Abs. The first ten amino acids in a V-region can and often do contain somatic hypermutations. A single amino acid change in this region can affect antibody binding.

In the innovative approach described herein, rather than amplifying V-regions using PCR primers for 5' V-region sequences, V-regions are amplified using leader sequence-specific forward primers. Because the leader sequence is just upstream of the V-region genes, all V-region sequences, including those with 5' end mutations, are amplified. The resulting library therefore contains a more complete V-region repertoire than those prepared by the conventional method (which results in the loss of all V-region sequences that are somatically hypermutated). Thus isolating low frequency V-regions that have been somatically mutated is possible. The reverse primers can be selected to allow amplification of all subclasses of an Ig isotype (e.g., gamma, mu, alpha, kappa, lambda, etc.), or the individual sub-classes of heavy chains (e.g., gamma3 or gamma 4) to have more focused libraries.

Expression of V-region nucleic acids amplified using leader sequence primers leads to the inclusion of leader peptides in the V-region protein product. When mammalian cells such as CHO cells are used to express these nucleic acids, endogenous post-translational processing mechanisms remove the leader peptide, allowing expression of the V-region or multiple V-region (e.g., heavy and light chain) constructs without the leader peptides interfering with Ag-binding screening assays. In bacterial phage display techniques, however, leader peptides are not removed. The presence of leader peptides can interfere in Ag-binding screening assays and thereby prevent detection of V-regions with high affinity for a target Ag.

To overcome this problem, the invention also provides for the creation of a second V-region library that is made using a larger than conventional set of 5' V-region primers ("Second Step" amplification). This larger set of primers allows a greater number of V-region sequences to be amplified compared to the number amplified using a traditional primer set. Of course, because these primers are designed to amplify germline sequences and not somatically mutated sequences, the primers themselves will introduce sequence errors in the amplification products (i.e., so that the somatic mutations are removed and substituted with germline sequences). After phage display is used to isolate those V-regions in scFv-expressing phage that bind target Ag, the nucleic acids encoding the identified V-regions are then sequenced. Using that sequence information, reverse primers that specifically amplify those nucleic acids are made and used along with leader sequence forward primers to amplify the V-regions from the first library to identify the actual and complete (somatic hypermutated) sequences of the Ag-specific V-regions that occur in the donor from which the first library was made.

In addition to the foregoing, a proteomics approach is also used wherein plasma IgG is isolated (e.g., using protein G chromatography followed by Ag-affinity chromatography). The resulting Ag-specific IgG mixture is further separated by capillary isoelectric focusing. The IgGs are then digested with proteases and the peptide fragment amino acid sequences are determined by mass spectrometry (MS). In the event that Second Step amplification fails to generate the appropriate somatic hypermutated V-region sequences (i.e., V-region germline primers failed to cross-hybridize/anneal with the desired 5' V-region sequence, which contained somatic mutated sequence from the first round amplification), de novo sequencing information of the isolated Ag-specific IgG can be used to perform nucleic acid sequencing of V-region products of the first round cDNA. Specifically, partial sequencing data from MS de novo protein sequencing is used to design V-region reverse primers. These reverse primers can be used together with leader sequence forward primers to identify and sequence the 5' ends of the V-region. Once these hypermutated regions have been identified, complete V-region sequences can be amplified using conventional PCR. These V-regions can then be assembled into complete, somatically hypermutated antibodies. MS peptide sequence information can also be used to corroborate that Ag-specific V-regions were correctly identified in the library screening process.

Accordingly, the invention features leader-specific primers for amplifying a nucleic acid encoding the V-region of a human immunoglobulin. The primers can include (a) a nucleic acid sequence that binds under stringent hybridization conditions to the complement of a nucleotide sequence selected from SEQ ID NOs:1-76, or (b) a nucleic acid sequence selected from SEQ ID NOs:1-76.

In another aspect, the invention features a set of leader-specific primers for amplifying at least 90% (e.g., at least 90, 91, 92, 93, 94, 95, 96, 97, 98, or 99%) of the nucleic acids encoding the V-region of a human immunoglobulin in a human tissue (e.g., peripheral blood) sample. The set can be one that amplifies 100% of the nucleic acids encoding the V-region of a human immunoglobulin in a human tissue sample. The set can include at least 50 different primers, and each of the different primers can include a different nucleic acid sequence, e.g., those of SEQ ID NOs:1-76. The set can also include at least 32 different primers, and each of the different primers can include a different nucleic acid sequence, e.g., those of SEQ ID NOs:1-32. The set can include at least 15 different primers, and each of the different primers can include a different nucleic acid sequence, e.g., those of SEQ ID NOs:33-48. The set can include at least 27 different primers, and each of the different primers can include a different nucleic acid sequence, e.g., those of SEQ ID NOs:49-76.

Also within the invention is a phage library that includes at least $10^5$ (e.g., at least $10^5$, $10^6$, or $10^7$) nucleic acid molecules encoding immunoglobulin heavy chains having somatic hypermutations in the first 8 amino acids of the variable region.

The invention further includes a purified antibody that includes a variable region sequence determined by screening a phage display library including variable region-encoding nucleic acid sequences isolated by PCR amplification of B lymphocytes isolated from a human subject using leader-specific primers.

In another aspect, the invention features a method that includes the steps of: (a) using a first PCR to amplify human immunoglobulin heavy and light chain nucleotide sequences from a human tissue sample including B lymphocytes, wherein leader-specific specific primers are used in the PCR amplification; (b) isolating the amplification products from the first PCR step; (c) creating a first set of constructs by inserting the isolated amplification products from the first PCR step into expression vectors; and (d) introducing the first set of constructs into a first set of host cells to create a first library of human immunoglobulin nucleotide sequences. In this method, the leader-specific primers can include a set of different polynucleotides each of which binds under stringent hybridization conditions to the complement of a different nucleic acid sequence selected from the group consisting of SEQ ID NOs:1-76. The method can also include one or more of the steps of: (e) using a second PCR to amplify human immunoglobulin nucleotide sequences from the first library or the human tissue sample, wherein variable region-specific specific primers are used in the PCR amplification; (f) isolating a second set of amplification products from the second PCR step; (g) creating a second set of constructs by inserting the second set of isolated amplification products into expression vectors; (h) introducing the second set of constructs into a second set of host cells to create a second library of human immunoglobulin nucleotide sequences; (i) screening the second library for a nucleotide sequence that encodes a variable region that specifically binds a target antigen; (j) obtaining the sequence of the nucleotide sequence that encodes a variable region that specifically binds a target antigen; (k) using the obtained sequence information to generate a reverse primer specific for the nucleotide sequence that encodes a variable region that specifically binds a target antigen; and (l) using the reverse primer and the leader specific primers in a third PCR to amplify a nucleotide sequence from the first library that corresponds to the sequence of an immunoglobulin in a B lymphocyte in the human tissue sample that promotes binding of the immunoglobulin to the target antigen. Proteomics can also be used in the methods of the invention as described herein.

Additionally within the invention is a human immunoglobulin cDNA library that includes a complete set of somatic hypermutated V-region sequences.

Unless otherwise defined, all technical terms used herein have the same meaning as commonly understood by one of ordinary skill in the art to which this invention belongs. Commonly understood definitions of biological terms can be found in Rieger et al., Glossary of Genetics: Classical and Molecular, 5th edition, Springer-Verlag: New York, 1991; and Lewin, Genes V, Oxford University Press: New York, 1994. Commonly understood definitions of medical terms can be found in Stedman's Medical Dictionary, $27^{th}$ Edition, Lippincott, Williams & Wilkins, 2000.

As used herein, an "antibody" or "Ab" is an immunoglobulin (Ig), a solution of identical or heterogeneous Igs, or a mixture of Igs. An "antibody" can also refer to fragments and engineered versions of Igs such as Fab, Fab', and F(ab')2 fragments; and scFv's, heteroconjugate Abs, and similar artificial molecules that employ Ig-derived CDRs to impart antigen specificity. A "monoclonal antibody" or "mAb" is an Ab expressed by one clonal B cell line or a population of Ab molecules that contains only one species of an antigen binding site capable of immunoreacting with a particular epitope of a particular antigen. A "polyclonal antibody" or "polyclonal Ab" is a mixture of heterogeneous Abs. Typically, a polyclonal Ab will include myriad different Ab molecules which bind a particular antigen with at least some of the different Abs immunoreacting with a different epitope of the antigen. As used herein, a polyclonal Ab can be a mixture of two or more mAbs.

An "antigen-binding portion" of an Ab is contained within the variable region of the Fab portion of an Ab and is the portion of the Ab that confers antigen specificity to the Ab (i.e., typically the three-dimensional pocket formed by the CDRs of the heavy and light chains of the Ab). A "Fab portion" or "Fab region" is the proteolytic fragment of a papain-digested Ig that contains the antigen-binding portion of that Ig. A "non-Fab portion" is that portion of an Ab not within the Fab portion, e.g., an "Fc portion" or "Fc region." A "constant region" of an Ab is that portion of the Ab outside of the variable region.

When referring to a protein molecule such as an Ab, "purified" means separated from components that naturally accompany such molecules. Typically, an Ab or protein is purified when it is at least about 10% (e.g., 9%, 10%, 20%, 30% 40%, 50%, 60%, 70%, 80%, 90%, 95%, 98%, 99%, 99.9%, and 100%), by weight, free from the non-Ab proteins or other naturally-occurring organic molecules with which it is naturally associated. Purity can be measured by any appropriate method, e.g., column chromatography, polyacrylamide gel electrophoresis, or HPLC analysis. A chemically-synthesized protein or other recombinant protein produced in a cell type other than the cell type in which it naturally occurs is "purified."

By "bind", "binds", or "reacts with" is meant that one molecule recognizes and adheres to a particular second molecule in a sample, but does not substantially recognize or adhere to other molecules in the sample. Generally, an Ab that "specifically binds" another molecule has a $K_d$ greater than about $10^5$, $10^6$, $10^7$, $10^8$, $10^9$, $10^{10}$, $10^{11}$, or $10^{12}$ liters/mole for that other molecule.

As used herein with respect to nucleic and amino acids, the term "percent sequence identity" means the number of exact matches between two aligned sequences divided by the length of the shorter sequences and multiplied by 100. Alignment of nucleic acid sequences can be performed as described in Smith and Waterman, Advances in Applied Mathematics 2:482-489 (1981), and for amino acid sequences as described in Dayhoff, Atlas of Protein Sequences and Structure, M. O. Dayhoff ed., 5 suppl. 3:353-358, National Biomedical Research Foundation, Washington, D.C., USA, and Gribskov (1986) Nucl. Acids Res. 14:6745. Two DNA sequences, or two polypeptide sequences are "substantially homologous" to each other when the sequences exhibit at least about 80%-85%, at least about 85%-90%, at least about 90%-95%, or at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., Molecular Cloning: A Laboratory Manual, Second Edition, (1989) Cold Spring Harbor, N.Y.; Nucleic Acid Hybridization: A Practical Approach, editors B. D. Hames and S. J. Higgins, (1985) Oxford; Washington, D.C.; IRL Press.

As used herein, the term "stringent hybridization conditions" means in 6× sodium chloride/sodium citrate (SSC) at 45° C., followed by washing in 0.2×SSC, 0.1% SDS at least 60° C.

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

BRIEF DESCRIPTION OF THE DRAWINGS

FIG. 1 is a schematic illustration of a step in a heavy chain PCR amplification strategy of the invention.

FIG. 2 is a schematic illustration of another step in the heavy chain PCR amplification strategy of the invention.

FIG. 3 is a schematic illustration of a step in a light chain PCR amplification strategy of the invention.

FIG. 4 is a schematic illustration of another step in the light chain PCR amplification strategy of the invention.

DETAILED DESCRIPTION

Figure 5:
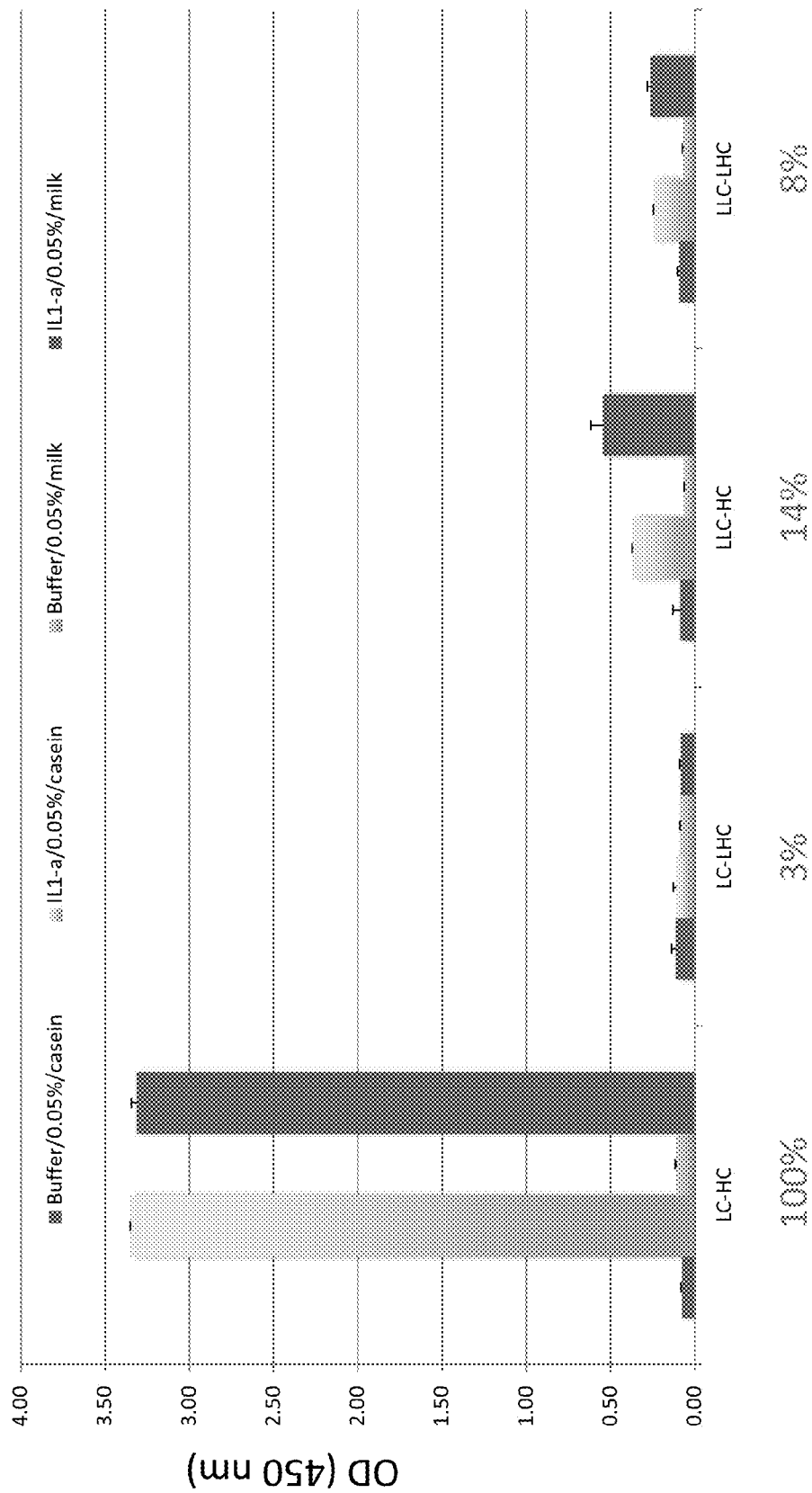
FIG. 5 is a graph showing that the presence of leader peptide upstream of either heavy chain variable or light chain variable region inhibited the ScFv fragment from binding to its antigen. The ScFv fragment containing leader on heavy chain (LC-LHC), leader on light chain (LLC-HC) and leaders on heavy and light chain (LLC-LHC) reduce binding to the antigen when compared to ScFv fragments with no leader (LC-HC).

The invention encompasses methods, compositions, and kits relating to the identification of human antibody sequences containing somatic hypermutations. The below described preferred embodiments illustrate adaptation of these methods, compositions, and kits. Nonetheless, from the description of these embodiments, other aspects of the invention can be made and/or practiced based on the description provided below.

General Methodology

Methods involving conventional immunological and molecular biological techniques are described herein. Immunological methods (for example, assays for detection and localization of antigen-Ab complexes, immunoprecipitation, immunoblotting, and the like) are generally known in the art and described in methodology treatises such as Current Protocols in Immunology, Coligan et al., ed., John Wiley & Sons, New York. Techniques of molecular biology are described in detail in treatises such as Molecular Cloning: A Laboratory Manual, 2nd ed., vol. 1-3, Sambrook et al., ed., Cold Spring Harbor Laboratory Press, Cold Spring Harbor, N.Y., 2001; and Current Protocols in Molecular Biology, Ausubel et al., ed., Greene Publishing and Wiley-Interscience, New York. Ab methods are described in Handbook of Therapeutic Abs, Dubel, S., ed., Wiley-VCH, 2007.

Overview

In traditional phage and yeast display methods for identifying Ag-specific Ig V-regions, PCR is used to amplify nucleic acid sequences corresponding to the V-regions of heavy and/or light Ig chains. The forward primers that initiate the PCR amplification process have a nucleic acid sequence that is the complement of the 5' germline end of each V-region so that cDNAs encoding the V-regions will be amplified. In the case where the 5' V gene segment differs from germline due to somatic hypermutation, this PCR process preferentially amplifies products that have the 5' germline sequence which leads to loss of diversity in phage and yeast display libraries.

In one aspect of the invention, V-regions are amplified using leader sequence-specific forward primers. Because the leader sequence is just upstream of the V-region genes, all V-region sequences, including those with extensive 5' end mutations, are amplified without loss of the original 5' V gene segment sequence. Libraries made with this method therefore contain a more complete V-region repertoire than those prepared by the conventional method. These libraries can be screened for Ag-specific V-regions using mammalian cells engineered to express the amplified V-region-encoding nucleic acids. Endogenous post-translational processing mechanisms remove the leader peptide, allowing expression of the V-region or multiple V-region (e.g., heavy and light chain) constructs without the leader peptides interfering with Ag-binding screening assays. In bacterial phage display techniques, where leader peptides can interfere in Ag-binding screening assays, the invention also provides for the creation of a second V-region library that is made using a larger than conventional set of 5' V-region primers. This larger set of primers allows a greater number of V-region sequences to be amplified compared to the number amplified using a traditional primer set, but as described above causes sequence errors to be introduced into the amplification products. Phage display is used to screen for those V-regions in scFv that bind the target Ag with high affinity. The nucleic acids encoding the identified V-regions are then sequenced, and, using that sequence information, reverse primers that specifically amplify those nucleic acids are made and used along with leader sequence forward primers to amplify the V-regions from the first library to identify the actual and complete sequences of the Ag-specific V-regions that occur in the donor from which the first library was made. Amino acid sequence information from fragments of donor Igs can be used to assist in the identification of nucleic acids encoding the heavy and light chains of donor Abs as well as to design PCR primers to amplify such nucleic acids.

PCR Primers

One aspect of the invention includes forward PCR primers for amplifying heavy and light chain human Ig V-regions from the nucleotides encoding their leader sequences. A set (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, or more) of such primers that can be used to amplify 100% of these sequences is preferred to capture low frequency V-regions, although a set of primers that captures less than 100% (e.g., 70-99, 70-75, 75-80, 80-85, 85-90, 90-95, or 95-99%) of these sequenced might also be used. An example of a set of these primers in set forth in Tables 1A, 1B, and 1C below. Using these primers sets (or a primer set with primers that are substantially homologous to those in Tables 1A, 1B, and 1C) and appropriate reverse primers, because the leader sequence is just upstream of the V-region genes, all V-region sequences, including those with extensive 5' end mutations, can be amplified.

TABLE 1A

Heavy chain Leader forward primers

```
NA-LH1-a-F    ATG GAC TGG ACC TGG AGG ATC CTC TTC [SEQ ID NO: 1]

NA-LH1-b-F    ATG GAC TGG ACC TGG AGG ATC CTC TTT TTG [SEQ ID NO: 2]

NA-LH1-c-F    ATG GAC TGG ACC TGG AGC ATC CTT TTC [SEQ ID NO: 3]

NA-LH1-d-F    ATG GAC TGC ACC TGG AGG ATC CTC [SEQ ID NO: 4]

NA-LH1-e-F    ATG GAC TGG ACC TGG AGA ATC CTC TTC TTG [SEQ ID NO: 5]

NA-LH1-f-F    ATG GAC TGG ACC TGG AGG GTC TTC [SEQ ID NO: 6]

NA-LH1-g-F    ATG GAC TGG ATT TGG AGG ATC CTC TTC TTG [SEQ ID NO: 7]

NA-LH2-a-F    ATG GAC ACA CTT TGC TCC ACG CTC [SEQ ID NO: 8]

NA-LH2-b-F    ATG GAC ACA CTT TGC TAC ACG CTC CTG [SEQ ID NO: 9]

NA-LH3-a-F    ATG GAA TTG GGG CTG AGC TGG G [SEQ ID NO: 10]

NA-LH3-b-F    ATG GAG TTG GGA CTG AGC TGG ATT TTC CTT [SEQ ID NO: 11]

NA-LH3-c-F    ATG GAG TTT GGG CTG AGC TGG GTT TTC CTT [SEQ ID NO: 12]

NA-LH3-d-f    ATG GAG TTG GGG CTG AGC TGG [SEQ ID NO: 13]

NA-LH3-e-F    ATG GAG TTT GGG CTG AGC TGG ATT [SEQ ID NO: 14]

NA-LH3-f-F    ATG GAG TTT GGG CTG AGC TGG GTT TT [SEQ ID NO: 15]

NA-LH3-g-F    ATG GAA CTG GGG CTC CGC TG [SEQ ID NO: 16]

NA-LH3-h-F    ATG GAG TTT GGG CTG AGC TGG C [SEQ ID NO: 17]

NA-LH3-i-F    ATG GAG TTT GGG CTG AGC TGG GTT [SEQ ID NO: 18]

NA-LH3-j-F    ATG GAG TTT GGA CTG AGC TGG GTT T [SEQ ID NO: 19]

NA-LH3-k-F    ATG GAG TTG GGG CTG TGC TGG [SEQ ID NO: 20]

NA-LH3-l-F    ATG GAG TTT GGG CTT AGC TGG GTT TTC [SEQ ID NO: 21]

NA-LH3-m-F    ATG GAG TTT TGG CTG AGC TGG GTT TTC [SEQ ID NO: 22]

NA-LH3-n-F    ATG ACG GAG TTT GGG CTG AGC TG [SEQ ID NO: 23]

NA-LH3-o-F    ATG GAG TTT GGG CTG AGC TGG G [SEQ ID NO: 24]

NA-LH4-a-F    ATG AAA CAC CTG TGG TTC TTC CTC CTG [SEQ ID NO: 25]

NA-LH4-b-F    ATG AAA CAC CTG TGG TTC TTC CTC CTC CTG [SEQ ID NO: 26]

NA-LH4-c-F    ATG AAG CAC CTG TGG TTC TTC CTC CTG [SEQ ID NO: 27]

NA-LH4-d-F    ATG AAA CAT CTG TGG TTC TTC CTT CTC CTG [SEQ ID NO: 28]

NA-LH4-e-F    ATG AAG CAC CTG TGG TTT TTC CTC CTG [SEQ ID NO: 29]

NA-LH5-a-F    ATG GGG TCA ACC GCC ATC CTC [SEQ ID NO: 30]
```

TABLE 1A-continued

Heavy chain Leader forward primers

| | | |
|---|---|---|
| NA-LH5-b-F | ATG GGG TCA ACC GCC ATC CTT G | [SEQ ID NO: 31] |
| NA-LH6-F | ATG TCT GTC TCC TTC CTC ATC TTC CTG C | [SEQ ID NO: 32] |

TABLE 1B

Kappa chain leader forward primers

| | | |
|---|---|---|
| NA-LK1-a-F | ATG GAC ATG AGG GTC CCC GC | [SEQ ID NO: 33] |
| NA-LK1-b-F | ATG GAC ATG AGG GTC CCT GCT CAG | [SEQ ID NO: 34] |
| NA-LK1-c-F | ATG GAC ATG AGA GTC CTC GCT CAG C | [SEQ ID NO: 35] |
| NA-LK1-d-F | ATG GAC ATG AGG GTC CTC GCT CAG | [SEQ ID NO: 36] |
| NA-LK1-e-F | ATG GAC ATG AGG CTG CCC GC | [SEQ ID NO: 37] |
| NA-LK1-f-F | ATA GAC ATG AGG GTC CCC GCT CAG | [SEQ ID NO: 38] |
| NA-LK2-a-F | ATG AGG CTC CCT GCT CAG CTC C | [SEQ ID NO: 39] |
| NA-LK2-b-F | ATG AGG CTC CTT GCT CAG CTT CTG G | [SEQ ID NO: 40] |
| NA-LK3-a-F | ATG GAA ACC CCA GCG CAG CTT C | [SEQ ID NO: 41] |
| NA-LK3-b-F | ATG GAA GCC CCA GCG CAG CT | [SEQ ID NO: 42] |
| NA-LK3-c-F | ATG GAA GCC CCA GCT CAG CTT CT | [SEQ ID NO: 43] |
| NA-LK3-d-F | ATG GAA CCA TGG AAG CCC CAG C | [SEQ ID NO: 44] |
| NA-LK4-F | ATG GTG TTG CAG ACC CAG GTC TTC ATT TC | [SEQ ID NO: 45] |
| NA-LK5-F | ATG GGG TCC CAG GTT CAC CTC C | [SEQ ID NO: 46] |
| NA-LK6-a-F | ATG TTG CCA TCA CAA CTC ATT GGG TTT CTG | [SEQ ID NO: 47] |
| NA-LK6-b-F | ATG GTG CCC TCG CTG CTC TTT C | [SEQ ID NO: 48] |

TABLE 1C

Lambda chain leader forward primers

| | | |
|---|---|---|
| NA-LL1-a-F | ATG GCC TGG TCC CCT CTC TTC CTC | [SEQ ID NO: 49] |
| NA-LL1-b-F | ATG GCC TGG TCT CCT CTC CTC AC | [SEQ ID NO: 50] |
| NA-LL1-c-F | ATG GCC AGC TTC CCT CTC CTC CTC | [SEQ ID NO: 51] |
| NA-LL1-d-F | ATG GCC GGC TTC CCT CTC CTC C | [SEQ ID NO: 52] |
| NA-LL1-e-F | ATG ACC TGC TCC CCT CTC CTC AC | [SEQ ID NO: 53] |
| NA-LL2-a-F | ATG GCC TGG GCT CTG CTC CTC | [SEQ ID NO: 54] |
| NA-LL2-b-F | ATG GCC TGG GCT CTG CTG CTC | [SEQ ID NO: 55] |
| NA-LL2-c-F | ATG GCC TGG GCT CTG CTA TTC CTC AC | [SEQ ID NO: 56] |
| NA-LL3-a-F | ATG GCA TGG ATC CCT CTC TTC CTC GGC | [SEQ ID NO: 57] |
| NA-LL3-b-F | ATG GCC TGG ACC GCT CTC CTT CTG | [SEQ ID NO: 58] |
| NA-LL3-c-F | ATG GCC TGG ACC CCT CTC CTG C | [SEQ ID NO: 59] |
| NA-LL3-d-F | ATG GCC TGG ATC CCT CTC CTG CTC | [SEQ ID NO: 60] |
| NA-LL3-e-F | ATG GCC TGG ACC CCT CTC TGG C | [SEQ ID NO: 61] |
| NA-LL3-f-F | ATG GCC TGG ACC GTT CTC CTC CTC | [SEQ ID NO: 62] |

TABLE 1C-continued

Lambda chain leader forward primers

| | | |
|---|---|---|
| NA-LL3-g-F | ATG GCA TGG GCC ACA CTC CTG C | [SEQ ID NO: 63] |
| NA-LL3-h-F | ATG GCC TGG ATC CCT CTC CTT CTC CC | [SEQ ID NO: 64] |
| NA-LL4-a-F | ATG GCC TGG GTC TCC TTC TAC CTA CTG C | [SEQ ID NO: 65] |
| NA-LL4-b-F | ATG GCC TGG ACC CAA CTC CTC CTC | [SEQ ID NO: 66] |
| NA-LL4-c-F | ATG GCC TGG ACC CCA CTC CTC C | [SEQ ID NO: 67] |
| NA-LL4-d-F | ATG GCT TGG ACC CCA CTC CTC TTC CTC | [SEQ ID NO: 68] |
| NA-LL5-a-F | ATG GCC TGG ACT CCT CTT CTT CTC TTG CTC | [SEQ ID NO: 69] |
| NA-LL5-b-F | ATG GCC TGG ACT CCT CTC CTC CTC C | [SEQ ID NO: 70] |
| NA-LL5-c-F | ATG GCC TGG ACT CTT CTC CTT CTC GTG C | [SEQ ID NO: 71] |
| NA-LL6-F | ATG GCC TGG GCT CCA CTA CTT CTC ACC | [SEQ ID NO: 72] |
| NA-LL7-F | ATG GCC TGG ACT CCT CTC TTT CTG TTC CTC | [SEQ ID NO: 73] |
| NA-LL8-F | ATG GCC TGG ATG ATG CTT CTC CTC GGA C | [SEQ ID NO: 74] |
| NA-LL9-F | ATG GCC TGG GCT CCT CTG CTC | [SEQ ID NO: 75] |
| NA-LL10-F | ATG CCC TGG GCT CTG CTC CTC | [SEQ ID NO: 76] |

In another aspect of the invention, a set of V-region PCR primers can be used to amplify nucleic acids encoding the heavy and light chain Ig variable regions. Preferred sets of such primers are those that allow a greater number of V-region sequences to be amplified compared to the number amplified using a traditional primer set. A set of such primers that can be used to amplify 100% of these sequences is preferred to capture low frequency V-regions, although a set of primers that captures less than 100% (e.g., 70-99, 70-75, 75-80, 80-85, 85-90, 90-95, or 95-99%) of these sequenced might all be used. Examples of sets of such primers are set forth in Tables 2 and 3 below. Using these primers sets (or a primer set with primers that are substantially homologous to those in Tables 2 and 3) and appropriate reverse primers, most if not all V-region sequences can be amplified by PCR, although this process introduces errors in those chains with hypermutated 5' V-regions (which can be corrected as described herein). For creation of scFv, each of the forward primers described herein can be engineered to include appropriate linker sequences such as the longlink sequence GGTGGTTCCTCTAGATCTTCCTCCTCTGGTGGCG-GTGGCTCGGGCGGTGGTGG G [SEQ ID NO: 176] (which can be located 5' to the primer sequence for the heavy chain and used with a suitable reverse primer such as SEQ NO:99 shown at the bottom of Table 2) or the linkers shown upstream of the primer sequences in SEQ ID NOs: 142-175 (used with the corresponding reverse primers such as SEQ ID NOs: 114, 133, and 134).

TABLE 2

| Primer name | Sequence |
|---|---|
| VH1a-F | CAG GTK CAG CTG GTG CAG TCT GG [SEQ ID NO: 77] |
| VH1b-F | CAG GTC CAG CTT GTG CAG TCT GG [SEQ ID NO: 78] |
| VH1c-F | SAG GTC CAG CTG GTA CAG TCT GG [SEQ ID NO: 79] |
| VH1d-F | CAR ATG CAG CTG GTG CAG TCT GG [SEQ ID NO: 80] |
| VH2a-F | CAG ATC ACC TTG AAG GAG TCT GG [SEQ ID NO: 81] |
| VH2b-F | CAG GTC ACC TTG ARG GAG TCT GG [SEQ ID NO: 82] |
| VH2c-F | CGG GTC ACC TTG AGG GAG TCT GG [SEQ ID NO: 83] |
| VH3a-F | GAR GTG CAG CTG GTG GAG TCT GG [SEQ ID NO: 84] |
| VH3b-F | CAG GTG CAG CTG GTG GAG TCT GG [SEQ ID NO: 85] |
| VH3c-F | GAG GTG CAG CTG TTG GAG TCT GG [SEQ ID NO: 86] |
| VH3d-F | GAG GTG CAG CTG GTG GAG [SEQ ID NO: 87] |
| VH3e-F | CAG GTG CAG CTG TTG GAG TCT GG [SEQ ID NO: 88] |
| VH3f-F | GAG GTG CAG CTG GTG GAG TCT GC [SEQ ID NO: 89] |

TABLE 2-continued

| Primer name | Sequence |
|---|---|
| VH3g-F | GAG GTG CAG CTG GTG GAG ACT GG [SEQ ID NO: 90] |
| VH3h-F | GAG GTG CAG CTG GTG GAG TCT CG [SEQ ID NO: 91] |
| VH4a-F | CAG STG CAG CTG CAG GAG TCS GG [SEQ ID NO: 92] |
| VH4b-F | CAG GTG CAG CTA CAG CAG TGG GG [SEQ ID NO: 93] |
| VH4c-F | CAG GTG CAG CTG CAG GAC TCG GG [SEQ ID NO: 94] |
| VH4d-F | CAG GTG CGG CTG CAG GAG TCG GG [SEQ ID NO: 95] |
| VH5-F | GAR GTG CAG CTG GTG CAG TCT GG [SEQ ID NO: 96] |
| VH6-F | CAG GTA CAG CTG CAG CAG TCA GG [SEQ ID NO: 97] |
| VH7-F | CAG GTS CAG CTG GTG CAA TCT GG [SEQ ID NO: 98] |
| Sfi-CH1@5'-R | CCTGGCCGGCCTGGCCACTAGT GAC CGA TGG GCC CTT GGT GGA [SEQ ID NO: 99] |

TABLE 3A

Kappa chain

[Note: R represents A or G at that position; Y represents C or T at that position; M represents A or C at that position; and S represents G or C at that position]

| Primer name | Sequence |
|---|---|
| Sfi-VK1a-F | GGGCCCAGGCGGCCRAC ATC CAG ATG ACC CAG TCT CC [SEQ ID NO: 142]<br>ATC CAG ATG ACC CAG TCT CC [SEQ ID NO: 100] |
| Sfi-VK1b-F | GGGCCCAGGCGGCCGMC ATC CAG TTG ACC CAG TCT CC [SEQ ID NO: 143]<br>ATC CAG TTG ACC CAG TCT CC [SEQ ID NO: 101] |
| Sfi-VK1c-F | GGGCCCAGGCGGCCGCC ATC CRG ATG ACC CAG TCT CC [SEQ ID NO: 144]<br>ATC CRG ATG ACC CAG TCT CC [SEQ ID NO: 102] |
| Sfi-VK1d-F | GGGCCCAGGCGGCCGTC ATC TGG ATG ACC CAG TCT CC [SEQ ID NO: 145]<br>ATC TGG ATG ACC CAG TCT CC [SEQ ID NO: 103] |
| Sfi-VK2a-F | GGGCCCAGGCGGCCGAT ATT GTG ATG ACC CAG ACT CCA C [SEQ ID NO: 146]<br>ATT GTG ATG ACC CAG ACT CCA C [SEQ ID NO: 104] |
| Sfi-VK2b-F | GGGCCCAGGCGGCCGAT RTT GTG ATG ACT CAG TCT CCA CTC [SEQ ID NO: 147]<br>RTT GTG ATG ACT CAG TCT CCA CTC [SEQ ID NO: 105] |
| Sfi-VK2c-F | GGGCCCAGGCGGCCGAG ATT GTG ATG ACC CAG ACT CCA C [SEQ ID NO: 148]<br>ATT GTG ATG ACC CAG ACT CCA C [SEQ ID NO: 106] |
| Sfi-VK3a-F | GGGCCCAGGCGGCCGAA ATT GTG TTG ACR CAG TCT CCA G [SEQ ID NO: 149]<br>ATT GTG TTG ACR CAG TCT CCA G [SEQ ID NO: 107] |
| Sfi-VK3b-F | GGGCCCAGGCGGCCGAA ATA GTG ATG ACG CAG TCT CCA G [SEQ ID NO: 150]<br>ATA GTG ATG ACG CAG TCT CCA G [SEQ ID NO: 108] |
| Sfi-VK3c-F | GGGCCCAGGCGGCCGAA ATT GTA ATG ACA CAG TCT CCA SCC [SEQ ID NO: 151]<br>ATT GTA ATG ACA CAG TCT CCA SCC [SEQ ID NO: 109] |
| Sfi-VK4-F | GGGCCCAGGCGGCCGAC ATC GTG ATG ACC CAG TCT CC [SEO ID NO: 152]<br>ATC GTG ATG ACC CAG TCT CC [SEQ ID NO: 110] |
| Sfi-VK5-F | GGGCCCAGGCGGCCGAA ACG ACA CTC ACG CAG TCT CC [SEQ ID NO: 153]<br>ACG ACA CTC ACG CAG TCT CC [SEQ ID NO: 111] |

TABLE 3A-continued

Kappa chain

[Note: R represents A or G at that position; Y represents C or T at that position; M represents A or C at that position; and S represents G or C at that position]

| Primer name | Sequence |
| --- | --- |
| Sfi-VK6a-F | GGGCCCAGGCGGCCGAA ATT GTG CTG ACT CAG TCT CCA GAC [SEQ ID NO: 154]<br>ATT GTG CTG ACT CAG TCT CCA GAC [SEQ ID NO: 112] |
| Sfi-VK6b-F | GGGCCCAGGCGGCCGAT GTT GTG ATG ACA CAG TCT CCA GCT [SEQ ID NO: 155]<br>GTT GTG ATG ACA CAG TCT CCA GCT [SEQ ID NO: 113] |
| Linker-CK@5'-R | GGAAGATCTAGAGGAACCACCGAA GAC AGA TGG TGC AGC CAC AGT [SEQ ID NO: 114] |

TABLE 3B

Lambda chain

| Primer name | Sequence |
| --- | --- |
| Sfi-VL1a-F | GGGCCCAGGCGGCCCAG TCT GTG CTG ACT CAG CCR CC [SEQ ID NO: 156]<br>TCT GTG CTG ACT CAG CCR CC [SEQ ID NO: 115] |
| Sfi-VL1b-F | GGGCCCAGGCGGCCCAG TCT GTG YTG ACG CAG CCR CC [SEQ ID NO: 157]<br>TCT GTG YTG ACG CAG CCR CC [SEQ ID NO: 116] |
| Sfi-VL1c-F | GGGCCCAGGCGGCCCAG TCT GTC GTG ACG CAG CCR CC [SEQ ID NO: 158]<br>TCT GTC GTG ACG CAG CCR CC [SEQ ID NO: 117] |
| Sfi-VL2-F | GGGCCCAGGCGGCCCAG TCT GCC CTG ACT CAG CCT SSC TC [SEQ ID NO: 159]<br>TCT GCC CTG ACT CAG CCT SSC TC [SEQ ID NO: 118] |
| Sfi-VL3a-F | GGGCCCAGGCGGCCTCC TAT GWG CTG ACT CAG CCA CYC [SEQ ID NO: 160]<br>TAT GWG CTG ACT CAG CCA CYC [SEQ ID NO: 119] |
| Sfi-VL3b-F | GGGCCCAGGCGGCCTCC TAT GAG CTG ACA CAG CYA CC [SEQ ID NO: 161]<br>TAT GAG CTG ACA CAG CYA CC [SEQ ID NO: 120] |
| Sfi-VL3c-F | GGGCCCAGGCGGCCTCT TCT GAG CTG ACT CAG GAC CC [SEQ ID NO: 162]<br>TCT GAG CTG ACT CAG GAC CC [SEQ ID NO: 121] |
| Sfi-VL3d-F | GGGCCCAGGCGGCCTCC TAT GAG CTG ATG CAG CCA CC [SEQ ID NO: 163]<br>TAT GAG CTG ATG CAG CCA CC [SEQ ID NO: 122] |
| Sfi-VL3e-F | GGGCCCAGGCGGCCTCC TAT GAG CTG ACA CAG CCA TCC TC [SEQ ID NO: 164]<br>TAT GAG CTG ACA CAG CCA TCC TC [SEQ ID NO: 123] |
| Sfi-VL3f-F | GGGCCCAGGCGGCCTCC TAT GAG CTG ACT CAG CCA CAC TC [SEQ ID NO: 165]<br>TAT GAG CTG ACT CAG CCA CAC TC [SEQ ID NO: 124] |
| Sfi-VL3g-F | GGGCCCAGGCGGCCTCC TCT GGG CCA ACT CAG GTG CC [SEQ ID NO: 166]<br>TCT GGG CCA ACT CAG GTG CC [SEQ ID NO: 125] |
| Sfi-VL4a-F | GGGCCCAGGCGGCCCAG CYT GTG CTG ACT CAA TCR YCC [SEQ ID NO: 167]<br>CYT GTG CTG ACT CAA TCR YCC [SEQ ID NO: 126] |
| Sfi-VL4b-F | GGGCCCAGGCGGCCCTG CCT GTG CTG ACT CAG CCC CC [SEQ ID NO: 168]<br>CCT GTG CTG ACT CAG CCC CC [SEQ ID NO: 127] |
| Sfi-VL5a-F | GGGCCCAGGCGGCCCAG SCT GTG CTG ACT CAG CCR BCT TCC [SEQ ID NO: 169]<br>SCT GTG CTG ACT CAG CCR BCT TCC [SEQ ID NO: 131] |
| Sfi-VL5b-F | GGGCCCAGGCGGCCCAG CCT GTG CTG ACT CAG CCA ACC TCC [SEQ ID NO: 170]<br>CCT GTG CTG ACT CAG CCA ACC TCC [SEQ ID NO: 132] |
| Sfi-VL6-F | GGGCCCAGGCGGCCAAT TTT ATG CTG ACT CAG CCC CAC [SEQ ID NO: 171]<br>TTT ATG CTG ACT CAG CCC CAC [SEQ ID NO: 128] |

TABLE 3B-continued

Lambda chain

| Primer name | Sequence |
|---|---|
| Sfi-VL7-F | GGGCCCAGGCGGCCCAG RCT GTG GTG ACT CAG GAG CC [SEQ ID NO: 172]<br>RCT GTG GTG ACT CAG GAG CC [SEQ ID NO: 129] |
| Sfi-VL8-F | GGGCCCAGGCGGCCCAG ACT GTG GTG ACC CAG GAG CC [SEQ ID NO: 173]<br>ACT GTG GTG ACC CAG GAG CC [SEQ ID NO: 130] |
| Sfi-VL9-F | GGGCCCAGGCGGCCCAG CCT GTG CTG ACT CAG CCA CC [SEQ ID NO: 174]<br>CCT GTG CTG ACT CAG CCA CC [SEQ ID NO: 177] |
| Sfi-VL10-F | GGGCCCAGGCGGCCCAG GCA GGG CTG ACT CAG CCA CC [SEQ ID NO: 175]<br>GCA GGG CTG ACT CAG CCA CC [SEQ ID NO: 178] |
| Linker-CL@5'1-R | GGAAGATCTAGAGGAACCACCCGT GGG GTT GGC CTT GGG CTG ACC [SEQ ID NO: 133] |
| Linker-CL@5'2-7-R | GGAAGATCTAGAGGAACCACCCGA GGG GGC AGC TTT GGG CTG ACC [SEQ ID NO: 134] |

The invention might also include a set of reverse PCR primers for amplifying the heavy and light chain human Ig V-regions from a sequence located 3' of the nucleotides encoding the V-region (e.g., nucleic acid sequences encoding a hinge or constant region). The reverse primers can be selected to allow amplification of all subclasses of an Ig isotype (e.g., gamma, mu, alpha, epsilon, kappa, lambda, etc.), or the individual sub-classes of heavy chains (e.g., gamma 1, gamma 2, gamma 3, gamma 4, alpha 1 and alpha 2) to have more focused libraries. The particular sequences of such reverse primers can be determined by one of skill in the art based on published sequences of the Ig isotype. Representative examples are shown in Table 4 below:

TABLE 4

| | | |
|---|---|---|
| All Heavy Chains | IgH-CH2-R | CCA CCA CCA CGC AYG TGA CC [SEQ ID NO: 135] |
| Lambda Light Chain | CL-R | CTT CTC CAC GGT GCT CCC TTC ATG CG [SEQ ID NO: 136] |
| Kappa Light Chain | CK-R | ACC CGA TTG GAG GGC GTT ATC CAC CT [SEQ ID NO: 137] |
| Isotype Specific | IgG1-Hinge-R<br>IgG2-Hinge-R<br>IgG3-Hinge-R<br>IgG4-Hinge-R | TGT GTG AGT TTT GTC ACA AGA TTT GGG CTC [SEQ ID NO: 138]<br>CGG TGG GCA CTC GAC ACA ACA TTT GCG CTC [SEQ ID NO: 139]<br>AGT TGT GTC ACC AAG TGG GGT TTT GAG CTC [SEQ ID NO: 140]<br>TGA TGG GCA TGG GGG ACC ATA TTT GGA CTC [SEQ ID NO: 141] |

Although the foregoing specific primers are preferred, other primers that hybridize to the complement of the specific sequences set forth herein under hybridization conditions used in PCR amplification or stringent hybridization conditions might also be used. For example, primers that have at least 75% (e.g., at least 80%, 85%, 90%, or 95%) sequence identity to, are substantially homologous to, and/or bind under stringent hybridization conditions to the complement of the specific sequences set forth herein. The length of these might range from about (+/−5 nucleotides) 15-100, 17-50, 18-40, or 20-30 nucleotides.

V-Region Libraries

The heavy and light chain Ig amplification products made using the foregoing primers in PCR can be used to create V-region libraries. For example, nucleic acids encoding Ig chains can be inserted into vectors, and the resulting constructs can be introduced into host cells (e.g., prokaryotic cells such as bacteria or eukaryotic cells such as yeast or mammalian cells) to make a library.

As one example, nucleic acids encoding naturally occurring Igs can be obtained from a donor sample containing B lymphocytes (e.g., peripheral blood mononuclear cells, isolated B cells or plasma cells, buffy coats, bone marrow, lymph node, spleen, or CNS samples). Typically, the samples are obtained from human donors previously determined to possess Abs specific for target Ags of interest (e.g., by ELISA or RIA). For identifying Abs to self Ags, preferred donors are those who have cytokine-specific autoantibodies (e.g., to interferon gamma, tumor necrosis factor alpha, interleukin 4 and interleukin 10, GM-CSF, erythropoietin, IL-6, IL-17, IL-22, interferon-α, interferon-β, IL-2, IL-8, vascular endothelial growth factor, and/or granulocyte-colony stimulating factor), and those with autoimmune diseases such as rheumatoid arthritis or lupus.

In one method, total RNA is extracted from these cells and reverse-transcribed using polyA primers. The resulting cDNA is used as template for PCR amplification using the primers described above and a suitable PCR strategy such as that described in the Examples below. The PCR products having the correct size can be visualized on agarose gels, excised, and purified. The purified products can then be digested with a suitable restriction enzyme (e.g., NotI or NcoI for the V heavy chain and SfiI or SalI for the V light chain). The digested fragments can again be gel purified and ligated with ligase (e.g., T4 DNA ligase) into a vector (e.g., a phagemid vector previously linearized with either NotI/ NcoI or SfiI/SalI). The ligated products can be electroporated into competent host cells (e.g., E. coli) to prepare heavy and light chain libraries. Isotype- and subclass-specific libraries can be made using reverse primers specific to the isotype or subclass.

Display Libraries

The heavy and light chain libraries can be used to create other libraries of cells that display Fabs, scFvs, or other Ab-like constructs that contain heavy and light chains. Such libraries can be created by isolation of the heavy and light chain-encoding nucleic acids by the above-described methods or by repurifying these nucleic acids from existing V-region libraries. By inserting the isolated heavy and light chain-encoding nucleic acids into suitable vectors and expressing these constructs in host cells, combinations of heavy and light chains can be assessed for Ag binding and/or subjected to multiple selection rounds to identify those which bind a target Ag with high affinity. These can be characterized by sequencing. See, e.g, Clackson et al., Nature 352:624-628, 1991; McCafferty et al., Nature 348: 552-554, 1990; and Kang et al., Proc. Nat'l Acad. Sci. 88:4363-4366, 1991.

For preparation of a scFv library, amplified VH and VL genes are gel-purified on agarose, and the scFv genes are assembled by overlap PCR using VH and VL fragments as templates. First, VH and VL are assembled with a linker by PCR without primers in which the short regions of complementarity at the ends of the linker promote hybridization of the various fragments. PCR performed, first in the absence of primers, and then after adding the outer primers. The scFv are digested with a suitable restriction enzyme, agarose gel-purified, and then ligated into a phage-display vector that had been cut with the same restriction enzyme. The ligated products are inserted (e.g., electroporated) into competent host cells (e.g., bacteria, yeast, or mammalian cells), and the cells are plated and cultured on suitable clones are then scraped off the plates into a suitable freezing medium and frozen (e.g., in superbroth medium with 10% glycerol at −70° C.). Fab libraries can be prepared in a similar fashion albeit without using a linker. Ag specific Fab and scFv can be obtained by screening bacterial phage display, yeast display, and/or mammalian cell display libraries techniques using selection methods such as panning, cell sorting, using an automated screener/picker (e.g., CLONEPIX™ systems), and magnetic bead separations.

Expression of V-region nucleic acids amplified using leader sequence primers leads to the inclusion of leader peptides in the V-region protein product. When mammalian cells such as CHO cells are used to express these nucleic acids, endogenous post-translational processing mechanisms remove the leader peptide, allowing expression of the V-region or multiple V-region (e.g., heavy and light chain) constructs without the leader peptides interfering with Ag-binding screening assays. In bacterial phage display techniques, however, leader peptides are not removed. The presence of leader peptides can interfere in Ag-binding screening assays and thereby prevent detection of V-regions with high affinity for a target Ag.

To overcome this problem, the invention also provides for the creation of a second V-region library that is made using a larger than conventional set of 5' V-region primers. This larger set of primers allows a greater number of V-region sequences to be amplified compared to the number amplified using a traditional primer set. Of course, because these primers are designed to amplify germline sequences and not somatically mutated sequences, the primers themselves will introduce sequence errors in the amplification products (i.e., so that the somatic mutations are removed and substituted with germline sequences). Phage display is used to screen for those V-regions in scFv that bind the target Ag with high affinity. The nucleic acids encoding the identified V-regions are then sequenced, and, using that sequence information, reverse primers that specifically amplify those nucleic acids are made and used along with leader sequence forward primers to amplify the V-regions from the first library (whose products were amplified with leader sequence primers) to identify the actual and complete sequences of the Ag-specific V-regions that occur in the donor from which the first library was made.

Ag-Specific Human mAbs or Other Ag-Targeting Constructs

The heavy chain and/or light chain V-regions (or portions thereof such as CDRs) identified as contributing to binding a particular target Ag can be used to make Ag-targeting constructs including full-length Abs, Ab fragments, engineered Abs, and fusion proteins. The full-length Abs and other Ag-targeting constructs can include non-V-regions sequences encoding Ig sequences specific to a particular isotype or subclass, e.g., IgG1, IgG2, IgG3, IgG4, IgD, IgA1, IgA2, IgE, or IgM. An Fab fragment may be a Fab', $F(ab)2$, $F(ab')_2$, $F(ab)_3$, Fv, scFv,), dsFv, Fd, or dAb Engineered Abs can be minibodies, diabodies, triabodies, tetrabodies, or kappa bodies. Ag-binding constructs can be made using recombinant or protein engineering techniques, e.g., wherein the V-regions or CDRs are grafted into the remaining portions of the constructs at the nucleic acid level.

Proteomics

In addition to the foregoing, a proteomics approach is also used wherein Ag-specific Abs in a donor tissue sample (e.g., plasma IgG) are isolated using known techniques (e.g., protein G, protein A, protein L, or ion exchange chromatography followed by Ag-affinity chromatography). The resulting Ag-specific Ab mixture is further separated, e.g., by capillary isoelectric focusing. The Igs are then digested with proteases and the peptide fragment amino acid sequences are determined by MS. The peptide sequence information can then be used to confirm that Ag-specific V-regions were correctly identified in the library screening process, and PCR primers can also be designed to amplify Ag-specific V-regions from the earlier prepared libraries.

Kits

One or more of the sets of PCR primers described herein and/or libraries described herein can be packaged in a kit which can include instructions for use.

EXAMPLES

Example 1: PCR Strategy

Referring now to FIG. 1, three rounds of PCR for heavy chain and two rounds of PCR for the light chain are performed. A cDNA library made from human PBMCs is used as a template, and first round of PCR is performed with the different leader forward primers (see Table 1A) and a reverse primer located in the CH2 region of the heavy chain. The size of the resulting PCR product is 905-1046 nucleotides depending on the subclass of IgGs. The second round of PCR uses the same forward primer as the first round, but reverse primers located in the hinge regions of the four different classes of IgG heavy chains using the reverse primers listed in Table 4. This step results in a sub-class specific heavy chain amplification. Referring to FIG. 2, the third PCR round for heavy chain uses forward primers located at the 5' end of the V-region (see Table 3) and a reverse primer located at the 5' end of the CH1 domain. The forward primers have adapters that introduce the long linker for the ScFv fragment and the reverse primer has an adapter that introduces the Sfi I site.

For the light chains, referring to FIG. 3, a PBMC cDNA library is also used as a template, and first round of PCR is performed using leader forward primers and reverse primers located in the Cκ and Cκ region of the kappa and lambda chains. The resulting PCR product is run on an agarose gel, and for the kappa chain, ~550 bp product is gel purified and used as a template in a second round PCR reaction. For the lambda chain, ~630 product is gel purified and used as a template for second round PCR reaction. The reverse primers are listed in Table 4. Referring to FIG. 4, the second round of PCR for light chain uses forward primers located at the 5' end of the V-region and a reverse primer located at the 5' end of the Cκ or Cλ domains. The forward primers have adapters that introduce the Sfi I site and the reverse primer has an adapter that introduces the long linker sequence.

Overlap extension PCR is performed, wherein the $3^{rd}$ round heavy chain products are mixed with equal ratios of kappa and lambda chain $2^{nd}$ round PCR products to generate overlap products. The overlap products are amplified using light chain adapter specific forward primers and heavy chain adapter specific reverse primer to generate ScFv fragments. The ScFv fragments are digested with Sfi I and cloned into the pComb3X vector.

Example 2: PCR Using V-region Primers

The following experiment was performed to test the effect of leader sequences on phage binding. A test ScFv fragment was generated with and without heavy and light chain leaders, and expressed on phages. The phages were used in an ELISA against specific antigens. FIG. 5 shows that the presence of leader peptide upstream of either heavy chain variable or light chain variable region inhibited the ScFv fragment from binding to its antigen.

Based on the above result, V-region specific primers are in the last round of PCR in which the long linker and Sfi I site are introduced. Once high affinity antigen-specific candidate ScFv fragments are sequenced, a primer is designed in the Framework 2 region as a reverse primer, and a leader specific forward primer is used on the $2^{nd}$ PCR product of heavy chain and the $1^{st}$ PCR product of the light chains, to obtain the correct 5' sequence of the V-region. The corrected V-region is used to generate full-length antibodies for biological activity assays.

Example 3: Discovery of Heavy and Light Chains that Bind a Human Cytokine

Using the methods and compositions described above human heavy and light chain genes encoding two different monoclonal antibodies against a human cytokine were identified. Both of these monoclonal antibodies exhibited high binding affinity for the antigen (in the nanomolar to picomolar range). This demonstrates that the methods and compositions of the invention are useful for identifying low frequency (in this case the antibodies were against a self antigen) antibodies from a human genome.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A library comprising at least $1\times10^5$ nucleic acid molecules encoding immunoglobulin heavy chains having somatic hypermutations in the first 8 amino acids of the variable region.

2. The library of claim 1, wherein the library comprises at least $1\times10^6$ nucleic acid molecules encoding immunoglobulin heavy chains having somatic hypermutations in the first 8 amino acids of the variable region.

3. The library of claim 1, wherein the library comprises at least $1\times10^7$ nucleic acid molecules encoding immunoglobulin heavy chains having somatic hypermutations in the first 8 amino acids of the variable region.

4. The library of claim 1, wherein the immunoglobulin heavy chains are human immunoglobulin heavy chains.

5. The library of claim 1, wherein the nucleic acid molecules are derived from a sample of human B lymphocytes.

* * * * *